United States Patent
Oren et al.

(10) Patent No.: US 12,042,262 B2
(45) Date of Patent: Jul. 23, 2024

(54) MAGNETIC FIELD DISTORTION DETECTION AND CORRECTION IN A MAGNETIC LOCALIZATION SYSTEM

(71) Applicant: St. Jude Medical International Holding S.á r.l., Luxembourg (LU)

(72) Inventors: Eitan Oren, Haifa (IL); Alon Izmirli, Ganot Hadar (IL); Adam Fischbach, Inver Grove Heights, MN (US); Charles B. Byrd, Oakdale, MN (US); Eric Betzler, Andover, MN (US); Scott Meyerson, Ham Lake, MN (US); Guy Hevel, Zicron Yaakov (IL); Adrian Herscovici, Haifa (IL); Roie Shlomovitz, Haifa (IL); Shay Levi, Kiryat Ata (IL); Nir Ben Dor, Givat Nili (IL)

(73) Assignee: ST JUDE MEDICAL INTERNATIONAL HOLDING, SA.R.L., Luxembourg (LU)

(*) Notice: Subject to any disclaimer, the term of this patent is extended or adjusted under 35 U.S.C. 154(b) by 1017 days.

(21) Appl. No.: 16/990,254

(22) Filed: Aug. 11, 2020

(65) Prior Publication Data

US 2020/0367785 A1 Nov. 26, 2020

Related U.S. Application Data

(62) Division of application No. 15/416,059, filed on Jan. 26, 2017, now Pat. No. 10,772,531.
(Continued)

(51) Int. Cl.
*A61B 5/06* (2006.01)
*A61M 25/01* (2006.01)
(Continued)

(52) U.S. Cl.
CPC ......... *A61B 5/062* (2013.01); *A61M 25/0127* (2013.01); *G01R 33/0017* (2013.01);
(Continued)

(58) Field of Classification Search
CPC .................. A61B 5/062; A61B 5/6852; A61B 2034/2051; A61B 2562/0223;
(Continued)

(56) References Cited

U.S. PATENT DOCUMENTS 6,233,476 B1  5/2001 Strommer et al.
6,498,944 B1  12/2002 Ben-Haim et al.
(Continued)

FOREIGN PATENT DOCUMENTS

EP  1878384 A2  1/2008
EP  1887309 A1  2/2008

OTHER PUBLICATIONS

T. Ju; S. Schaefer, J. Warren, "Mean Value Coordinates for Closed Triangular Meshes," ACM Transactions on Graphics, Jul. 2005, 24(3): 561-566.

*Primary Examiner* — Baisakhi Roy
*Assistant Examiner* — Kaitlyn E Sebastian
(74) *Attorney, Agent, or Firm* — Billion & Armitage

(57) ABSTRACT

A method for detecting and correcting for magnetic field distortions within a magnetic field used for medical magnetic localization systems may include a first set of one or more signals is indicative of the magnetic field sensed by each of the sensor coils within the metal distortion detection fixture at a first time received from the metal distortion detection fixture. A first magnitude value of the combined signals is determined. A second set of one or more signals is indicative of the magnetic field sensed by each of the sensor coils at a second time is received and a second magnitude value of the combined signals is determined. A magnetic
(Continued)

shift in the magnetic field between the first and second magnitude values is determined. The magnetic shift is compared to a threshold shift amount indicative of a magnetic distortion in the magnetic field.

12 Claims, 7 Drawing Sheets

Related U.S. Application Data

(60) Provisional application No. 62/331,294, filed on May 3, 2016, provisional application No. 62/331,338, filed on May 3, 2016, provisional application No. 62/287,383, filed on Jan. 26, 2016.

(51) Int. Cl.
    *G01R 33/00*      (2006.01)
    *G01R 33/02*      (2006.01)
    *A61B 5/00*      (2006.01)
    *A61B 34/20*      (2016.01)

(52) U.S. Cl.
    CPC ............ *G01R 33/02* (2013.01); *A61B 5/6852* (2013.01); *A61B 2034/2051* (2016.02); *A61B 2562/0223* (2013.01); *A61B 2562/17* (2017.08)

(58) Field of Classification Search
    CPC ........... A61B 2562/17; A61M 25/0127; G01R 33/0017; G01R 33/02
    See application file for complete search history.

(56) References Cited

U.S. PATENT DOCUMENTS

| | | | |
|---|---|---|---|
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 * | 6/2008 | Strommer | A61B 5/062 600/428 |
| 7,902,816 B2 * | 3/2011 | Shechter | A61B 5/06 324/207.17 |
| 9,326,702 B2 | 5/2016 | Eichler et al. | |
| 2005/0107687 A1 | 5/2005 | Anderson | |
| 2007/0060833 A1 | 3/2007 | Hauck | |
| 2008/0183064 A1 | 7/2008 | Chandonnet et al. | |
| 2010/0331671 A1 | 12/2010 | Martinelli | |
| 2011/0156700 A1 * | 6/2011 | Kariv | A61B 5/062 324/244 |
| 2012/0092004 A1 | 4/2012 | Billeres | |
| 2012/0265054 A1 | 10/2012 | Olson | |
| 2013/0066193 A1 | 3/2013 | Olson et al. | |
| 2017/0209072 A1 * | 7/2017 | Oren | G01R 33/02 |

* cited by examiner

MAGNETIC FIELD DISTORTION DETECTION AND CORRECTION IN A MAGNETIC LOCALIZATION SYSTEM

CROSS-REFERENCE TO RELATED APPLICATIONS

This application is a divisional of U.S. patent application Ser. No. 15/416,059, filed 26 Jan. 2017, which claims the benefit of U.S. provisional application No. 62/287,383, filed 26 Jan. 2016; U.S. provisional application No. 62/331,294, filed 3 May 2016; and U.S. provisional application No. 62/331,338, filed 3 May 2016, all of which are hereby incorporated by reference as though fully set forth herein.

BACKGROUND a. Field

The present disclosure relates generally to the magnetic localization of medical instruments within a human body. More specifically, the instant disclosure relates to detecting magnetic field distortions within a magnetic field used for such magnetic localization systems.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which may be used for diagnosis, mapping, ablation, or other treatments. Precise positioning of the catheters and clinician knowledge of the precise location within the body of the patient is desirable for improved procedure success rates.

To position a catheter within the body at a desired site, some type of localization must be used. To determine the relative position of the catheter to patient anatomy, magnetic localization systems have been developed that provide a location of the catheter within a well-known and controlled magnetic field. The externally-generated magnetic fields include precise magnetic gradients (field lines) that are sensed by the catheter (e.g., by elements such as coils) being located within the magnetic field. The currents induced by the magnetic field(s) in the sensors are analyzed using algorithmic processes and used to determine the position of the catheter within the patient's body. Once the catheter is positioned within the patient, as desired, a clinician may operate the catheter, for example, to ablate tissue to interrupt potentially pathogenic heart rhythms.

However, magnetic localization systems are susceptible to error induced by magnetic distortions within the magnetic field caused by, for example, extraneous ferrous or metallic objects intruding into the magnetic field. The introduction of such distortions may result in the system presenting an inaccurate position of the catheter within the patient's body. Such inaccurate catheter location data can limit the efficacy of a medical procedure.

The foregoing discussion is intended only as an exemplary illustration of the present field and is not intended to limit the claim scope.

BRIEF SUMMARY

Various embodiments of the present disclosure identify and correct for magnetic field distortions associated with the intrusion of metallic objects in a magnetic field used for localization of a medical device.

Various embodiments of the present disclosure are directed to systems for detecting magnetic distortion in a magnetic field used for localizing a catheter within a patient. In one exemplary embodiment, the system includes one or more metal distortion fixtures, and processor circuitry. The metal distortion fixture includes more than one sensor coil positioned at fixed distances and orientations relative to one another. Each of the sensor coils senses the magnetic field aligned with the orientation of the sensor and outputs an electrical signal indicative of the sensed magnetic field. The processor circuitry is communicatively coupled to the metal distortion fixture, and receives the electrical signals from each of the sensor coils, calculates a time-dependent magnetic field magnitude value for each of the received signals, and detects magnetic distortion. In yet further more specific embodiments, the processor circuitry calculates a magnetic shift in the magnetic field between a first magnitude value at a first time and a second magnitude value at a second time, later than the first time, by comparing the two magnitude values and determining a change in magnitude value over time. The calculated shift is then compared to a threshold shift amount indicative of a distortion that will impede the efficacy of the catheter localization within the patient.

Various embodiments of the present disclosure are directed to apparatuses for detecting electronic signals indicative of magnetic distortion in a magnetic field for localization of a catheter within a patient. In one exemplary embodiment, the apparatus includes a first sensor coil, a second sensor coil oriented orthogonally to the first sensor coil and fixedly positioned relative to the first sensor coil, and a third sensor coil oriented orthogonally to the first and second sensor coils and fixedly positioned relative to the first and second sensor coils. The first, second, and third sensor coils receive energy indicative of a magnetic field strength and magnetic field orientation substantially coaxial with the receiving sensor coil. In yet further more specific embodiments, each of the coils converts energy from the magnetic field into an electrical signal, and variation of the electrical signal output of the sensor coil over time may be indicative of a change in the magnetic field associated with the introduction of a ferrous object into the magnetic field.

Various embodiments of the present disclosure are directed to methods for detecting magnetic distortion in a magnetic field for localization of a catheter within a patient. In one exemplary embodiment, the method includes receiving a first set of one or more signals from a metal distortion sensor indicative of the magnetic field sensed by each of the sensor coils within the metal distortion sensor at a first time. Based on the first set of signals, a first magnitude value of the combined signals indicative of a magnetic field at the first time is determined. After a time, a second set of one or more signals from the metal distortion sensor indicative of the magnetic field sensed by each of the sensor coils at a second time are received, and a second magnitude value of the combined signals indicative of another magnetic field at the second time is determined. Based on the first and second magnitude values, a magnetic shift is determined and compared a threshold shift amount indicative of a magnetic distortion in the magnetic field that causes a substantial variation between the perceived location of the catheter within the patient and the actual location at a given time.

Additional features, advantages, and embodiments of the disclosure may be set forth or apparent from consideration of the detailed description and drawings. Moreover, it is to be understood that the foregoing brief summary and the following detailed description, drawings, and attachment are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure.

Figure 1:
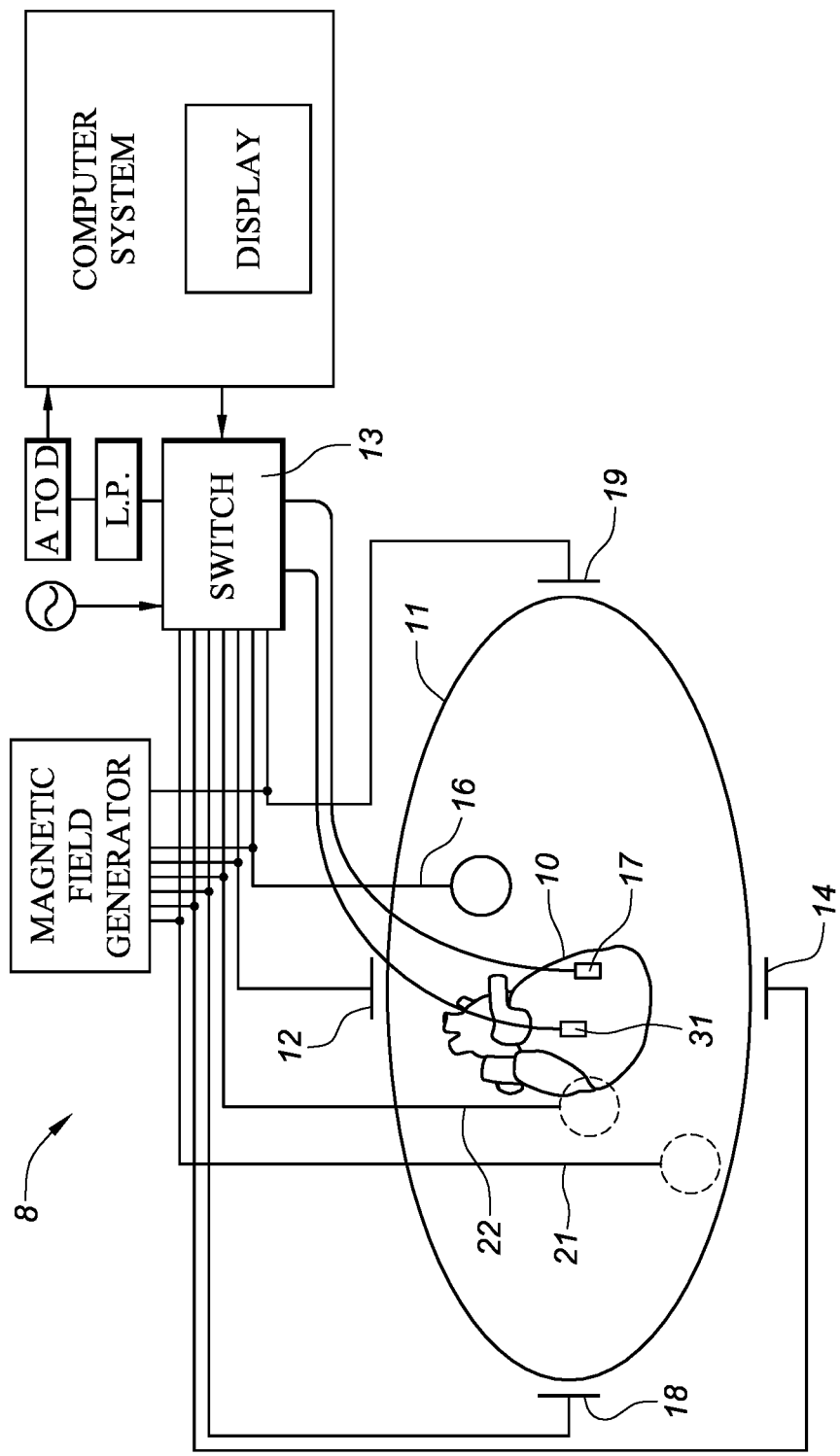
FIG. 1 is a schematic diagram of a magnetic localization system, consistent with various aspects of the present disclosure.

While various embodiments discussed herein are amenable to modifications and alternative forms, aspects thereof have been shown by way of example in the drawings and will be described in further detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

Cardiac localization systems are capable of displaying a three-dimensional (3D) position of conventional electrophysiology catheters within an overlaid model or image of a cardiac chamber. These localization systems may also display cardiac electrical activity as waveform traces and as dynamic 3-D isopotential maps on the model of the cardiac chamber. The contoured surfaces of these three dimensional models are based on the anatomy of the patient's own cardiac chamber. These localization systems may use impedance based and/or magnetic based localization technologies to render catheter position and model creation.

When using magnetic localization, the magnetic fields generated from a local source are inherently susceptible to distortions caused by metallic or ferrous objects intruding into, or being placed adjacent to, the generated magnetic fields. Such distortions can cause inaccuracies in calculated or determined medical device locations and in related anatomical models and other representations.

Magnetic sensors embedded within intracardiac catheters are used to determine position and orientation of the catheter with respect to one or more known reference positions. This magnetic position and orientation information can be used to navigate the catheter and can also be used to optimize impedance-based catheter localization. When navigating catheters in magnetic space, the displayed or otherwise reported positions of the catheters can notably shift (e.g., visually shift on a screen displaying a representation of the location of the catheters) when the underlying magnetic field is changed/distorted despite no actual change (or minimal actual change) in the catheter's physical location. Understandably, this shift can cause inaccuracies to models created using the reported locations of the catheters. Magnetic position and orientation data from catheters can also be used in conjunction with impedance-based localization technologies and used to optimize/scale non-linear impedance fields. Embodiments of the present disclosure, as described in more detail below with reference to the figures, identify the existence of such distortions within a magnetic field.

FIG. 1 shows a schematic diagram of a magnetic localization system 8 used for navigating the human anatomy of a patient 11 (depicted, for simplicity's sake, as an oval in FIG. 1) while conducting a medical procedure. For example, as shown in FIG. 1, the system 8 may be used to map a heart 10 of the patient and to navigate a cardiac catheter through the chambers of the heart. Magnetic localization system 8 determines the location (and, in some embodiments, the orientation) of objects (e.g., a portion of a diagnostic or ablation catheter, such as the electrode assembly 112 depicted in FIGS. 2A and 2B), typically within a three-dimensional space, and expresses those locations as position information determined relative to at least one reference. Specifically, the magnetic localization system 8 can be used to determine the location of the cardiac catheter within a magnetic field, which is then overlaid onto, for example, an image or a model of the heart 10. In other embodiments, magnetic resonance imaging data, among other reference data may be overlaid onto the three-dimensional space to provide a clinician with a virtual work environment in which to reference for real-time position of the cardiac catheter relative to the patient's heart 10.

The magnetic localization system 8 may include various visualization, localization, mapping, and navigation components. For example, the localization system 8 may comprise a magnetic-field-based system such as the CARTO™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the localization system 8 may comprise a magnetic field based system such as the MEDIGUIDE™ Technology system available from St. Jude Medical, Inc., and as generally shown with reference to one or more of U.S. Pat. Nos. 6,233,476; 7,197,354; 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/IB2014/059709 entitled "Medical Device Navigation System" filed on 13 Mar. 2014, the disclosures of which are hereby incorporated by reference in their entireties as though fully set forth herein. In yet another embodiment, the localization system 8 may comprise a hybrid electric-field-based and magnetic-field-based system, such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set fully forth herein, or the CARTO™ 3 system commercially available from Biosense Webster. In yet still other exemplary embodiments, the localization system 8 may comprise or be used in conjunction with other commonly available systems, such as, for example and without limitation, fluoroscopic, computed tomography (CT), and magnetic resonance imaging (MRI)-based systems. For purposes of clarity and illustration only, the localization system 8 will be described hereinafter as comprising a magnetic-based localization system.

Various embodiments of the present disclosure may include various visualization, mapping and navigation components as known in the art, including, for example, an EnSite™ NavX™ Electro Anatomical Mapping System commercially available from St. Jude Medical, Inc., or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application). The '397 patent and the '580 application are both hereby incorporated by reference as though fully set forth herein.

FIG. 1 may further exemplify a hybrid localization system including two localization systems: an impedance-based localization system and a magnetic-based localization system.

In general, and as shown in FIG. 1, localization system 8 includes a plurality of magnetic field transmitters (e.g., 12, 14, 16, 18, 19, and 21) that emit a magnetic field across the patient's body 11. These magnetic field transmitters, which may be placed upon or attached/applied to the patient, or fixed to an external apparatus, define three generally orthogonal axes, e.g., an x-axis, a y-axis, and a z-axis. The magnetic field transmitters are electrically coupled to a magnetic field generator. The magnetic field generator generates one or more magnetic fields that may be transmitted simultaneously, time multiplexed, and/or frequency multiplexed via the magnetic field transmitters. A switch 13 samples the signals received from one or more of receivers 17, 22, and 31 (e.g., a catheter, a patient reference sensor, an internal reference sensor, a metal distortion sensor, etc.). The received signals from the receivers, indicative of the magnetic field that traversed through the patient's body 11 from one or more of the transmitters, are then converted from an analog to a digital signal for further processing by the computer system. The computer system performs computations on the data received from the receivers to determine, for example, the location of a cardiac catheter within the patient's heart. However, the actual catheter position may be obscured by magnetic distortions within the magnetic field caused by other ferrous/metallic bodies. These magnetic distortions are associated with an error rate of the perceived position of the catheter compared to the actual position of the catheter.

For reference by a clinician during a procedure, the perceived location of the catheter within the magnetic field can be presented on a display in relation to known reference points, e.g., cardiac chambers, arteries, etc.

For purposes of this disclosure, an exemplary medical device, such as a catheter may extend into the left ventricle of the patient's heart 10. The catheter includes a plurality of sensor coils spaced along its length. As used herein, the term "sensor coils" generically refer to any element whose position within a magnetic field can be measured by that system (e.g., magnetic sensors). Because each sensor coil lies within the magnetic field, localization data may be collected simultaneously for each sensor coil.

A magnetic-based localization system 8 may include a fixed reference 22 to define the origin of the magnetic-based localization system's coordinate frame. This fixed reference provides a relative position to which the positions of sensor coils on the catheter are measured. Such a fixed reference can likewise be in a fixed internal or external location. Likewise, multiple references may be used for the same or different purposes (e.g., to correct for respiration, patient shift, system drift, or the like).

A computer system, which can comprise a conventional general-purpose computer, a special-purpose computer, a distributed computer, or any other type of computer, and which can comprise one or more processors, such as a single central processing unit (CPU), or a plurality of processing units, commonly referred to as a parallel processing environment, may control magnetic localization system 8 and/or execute instructions to practice the various aspects of the embodiments described herein.

Figures 2A, 2B:
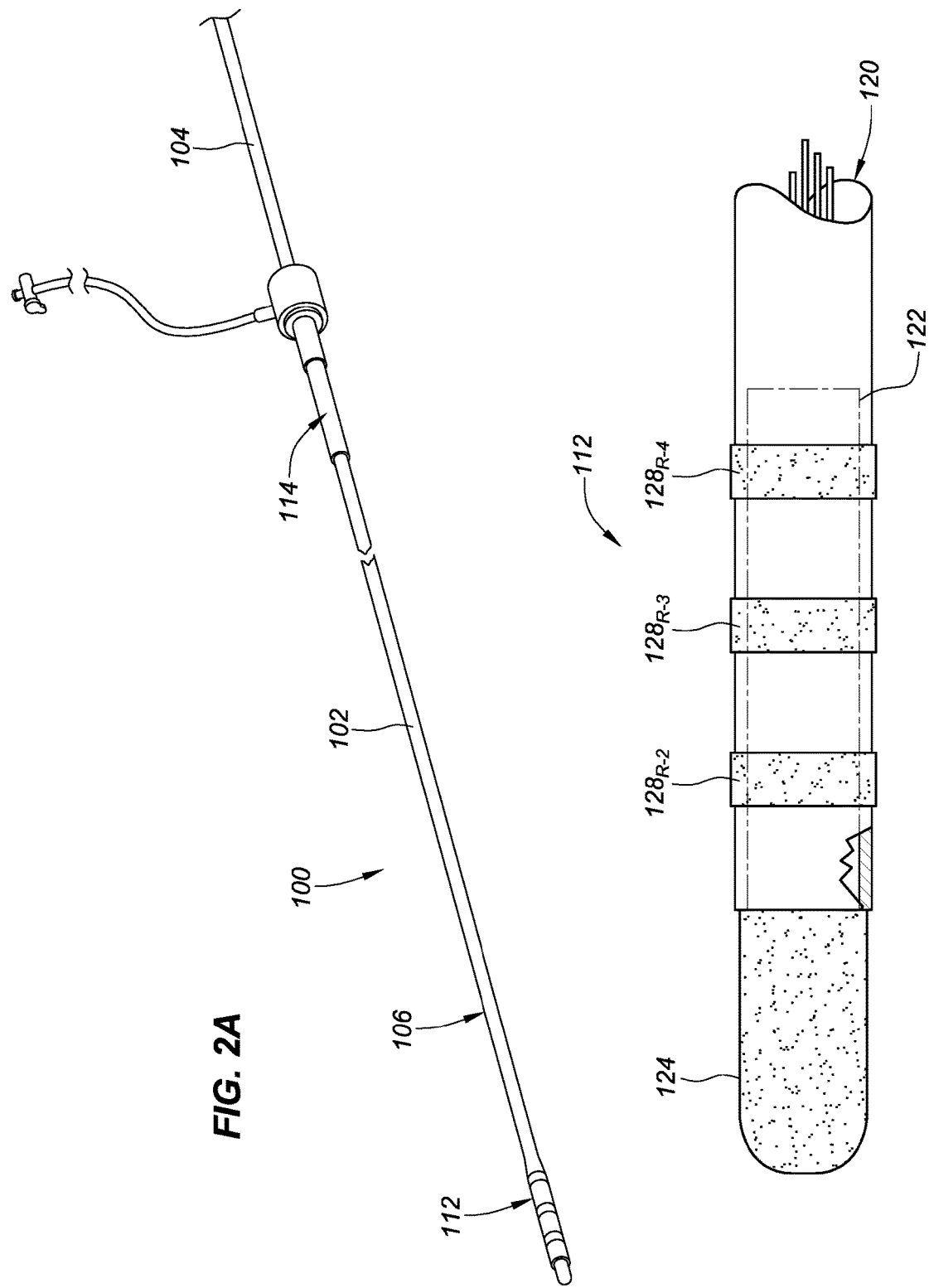
FIG. 2A is a fragmentary, isometric view of a catheter assembly comprising a catheter configured for localization in a magnetic localization system and an introducer, consistent with various aspects of the present disclosure.
FIG. 2B is an enlarged, fragmentary side view of the distal tip assembly of the catheter of FIG. 2A, consistent with various aspects of the present disclosure.

FIG. 2A is a simplified, isometric view of a single-use catheter assembly 100, comprising a catheter 106 that includes a catheter tip assembly (or an electrode assembly or distal tip assembly) 112 at a distal end portion and operatively adapted for conducting a diagnostic or a therapeutic procedure under clinician control. A proximal end portion 104 of the catheter 106 may include a steering handle or other mechanism (not shown). In the present embodiment, catheter 106 is a mapping catheter. The catheter 106 includes a flexible shaft 102 extending between the proximal end portion 104 and the catheter tip assembly 112. The catheter assembly 100 further includes an electrical connector (not shown) configured to establish electrical connection(s) between the catheter tip assembly 112 and external electrical components (not shown) to perform, for example, localization, mapping, ablation, and/or pacing procedures. FIG. 2A further shows an introducer 114 comprising part of the catheter assembly 100. The catheter tip assembly 112 may comprise a plurality of sensors coils (or localization coils or sensors) such as those shown schematically in, for example, FIGS. 3A, 3B, and 3C of the present application, or the sensors shown in U.S. Pat. No. 6,690,963 (see, e.g., sensors 30, 32, 34 depicted in FIGS. 2 and 3), which has been incorporated herein by reference. These localization coils may be located, for example, in the region shown by the dashed box 122 in FIG. 2B.

FIG. 2B is an enlarged, side view showing, in greater detail, the tip assembly 112. The tip assembly 112 includes a tip electrode 124 (schematically shown in FIG. 2B); a plurality of ring electrodes 128R-2, 128R-3, and 128R-4; and a plurality of electrical conductors 120 (e.g., one conductor electrically connected to each of the three ring electrodes and a separate conductor electrically connected to the tip electrode 124). Additional electrical connectors may extend proximally from the tip assembly 112 if localization coils are located in, for example, the area outlined by dashed box 122.

Figure 3A:
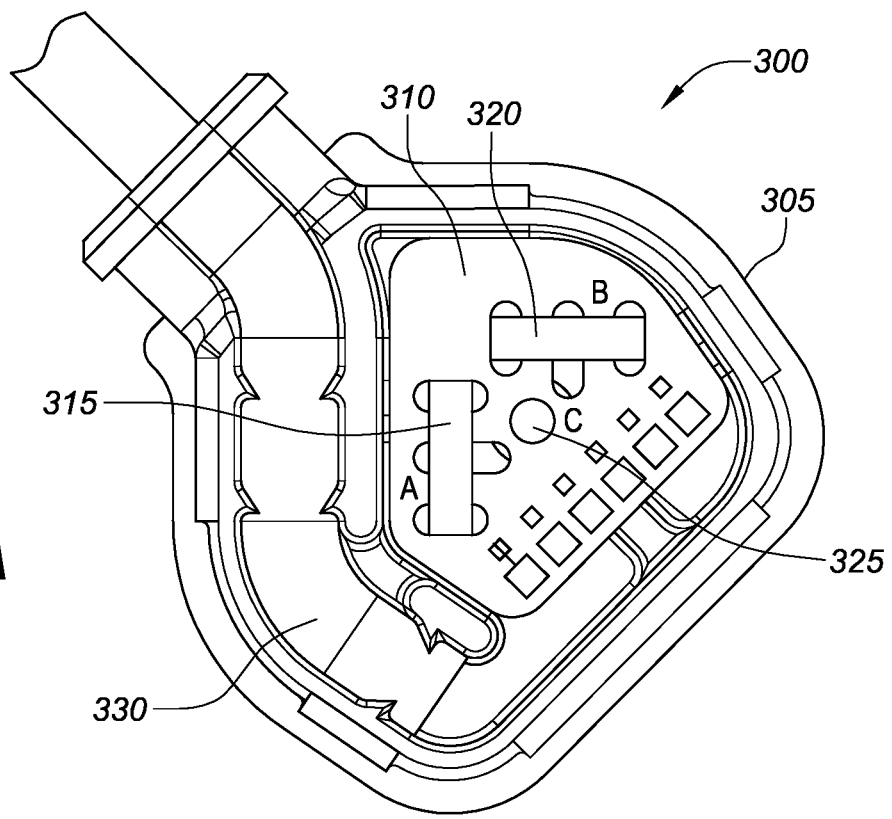
FIG. 3A is a top view of a magnetic detection sensor, consistent with various aspects of the present disclosure, with portions of the sensor housing broken away to reveal internal features.
Figure 3B:
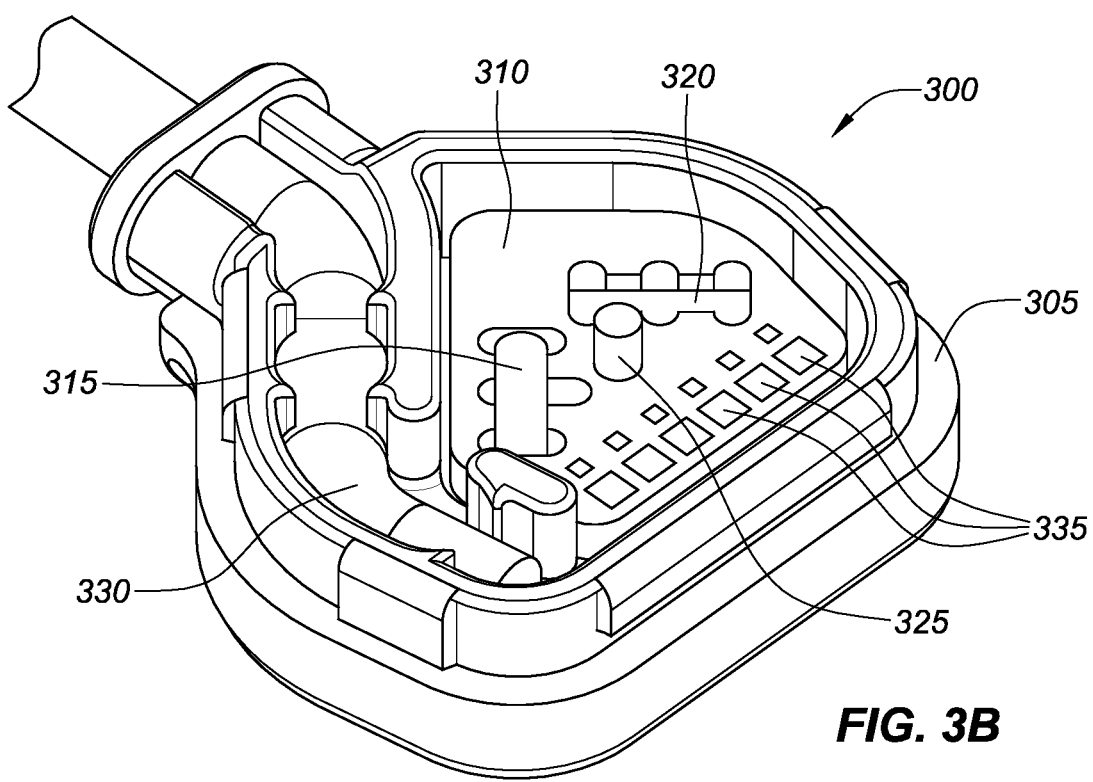
FIG. 3B is an isometric view of the magnetic detection sensor of FIG. 3A, consistent with various aspects of the present disclosure.

FIGS. 3A and 3B are views of a metal distortion sensor 300 including a circuit board 310 that is electrically coupled to first, second, and third sensor coils 315, 320, and 325, respectively. Each of the sensor coils are affixed relative to the metal distortion sensor housing 305 and the circuit board 310, with the sensor coils fixed, at least in this embodiment, in orthogonal orientations relative to one another. During operation, the metal distortion sensor 300 is placed within a generated magnetic field and each of the respective sensor coils receive energy indicative of the strength and orientation of the magnetic field. In one specific embodiment, a vector sum of the received energy is computed to determine a perceived change in the position of the sensor coils relative to one another. A perceived change being indicative of a magnetic distortion in the magnetic field proximal the metal distortion sensor. In medical magnetic localization applications (as discussed in more detail above), such magnetic distortions affect the ability of the system to accurately locate a position of, for example, a catheter within the patient's body.

Before transmitting the received signals from the first, second, and third sensor coils 315, 320, and 325, respectively, to computing circuitry for processing and for determination of the amount of distortion in the magnetic field, circuitry within circuit board 310 may conduct a number of signal processing functions including, e.g., analog-to-digital conversion, pre-amplification, and signal noise filtration. After signal processing, the received signals are transmitted to magnetic localization system processor circuitry via cable 330 which is coupled to the circuit board 310 via bonding pads 335. In further embodiments, the metal distortion sensor may wirelessly transmit the received signals from each of the sensor coils to the processor circuitry of the magnetic localization system using wireless data transmission protocols known to one of skill in the art.

Figure 3C:
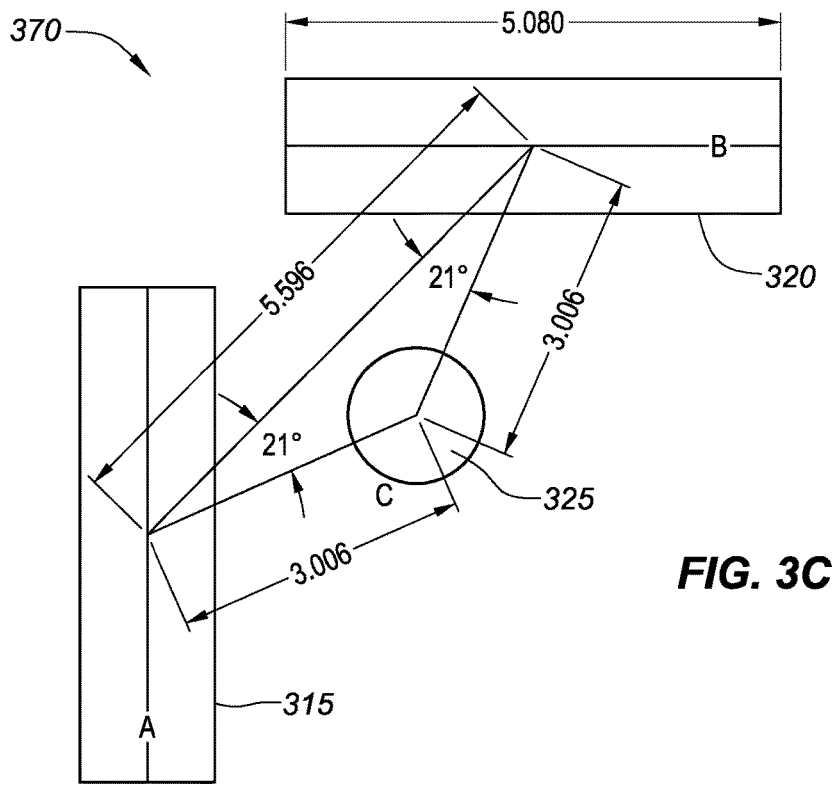
FIG. 3C is an enlarged top view of an embodiment of a sensor coil array configuration broken away from, for example, the magnetic detection sensor of FIGS. 3A and 3B, consistent with various aspects of the present disclosure.

FIG. 3C shows an exemplary sensor coil array 370 (including first, second, and third sensor coils, 315, 320, and 325, respectively), exploded away from the housing 305, circuit board 310, and other components shown in FIGS. 3A and 3B. As shown in FIG. 3C, the sensor coils are oriented orthogonal to one another and affixed at precise distances from each other. During operation of the metal distortion sensor in a magnetic field, the output of the sensor coil array is used to calculate magnitude positions and orientations associated with the mechanical position and orientation of the sensor coils relative to one another. In one specific embodiment, for example, the vector sum of the distances are calculated between the centers of the longitudinal axes of the three sensor coils. In response to a distortion in the magnetic field, the perceived location of one (or more) of those sensor coils may be displaced from its known/fixed location relative to the other sensor coils. As a result, the corresponding vector sum would be correspondingly affected. A change in the vector sum from the initial index value, above a determined threshold, is indicative of a distortion to the generated magnetic field which is unreliable. After determining an initial index-value (where the magnetic field is free of distortions), subsequent magnitude positions and orientations may be correlated timewise. These later magnitude values may vary from the initial index-value due to localized magnetic distortions within the magnetic field, resulting in a perceived skewing of the location and orientation of the sensor coils relative to one another (even though the orientation and position of the sensor coils to one another are fixed). The initial index-value may be compared to subsequent index-values to determine when acceptable levels of magnetic field distortion during a medical procedure are exceeded. This delta value (the change in value between the initial index-value and a subsequent index-value) is associated with distortion related drift in the localization of the catheter.

In one exemplary embodiment, an acceptable delta value for magnetic distortion may be determined by the clinician (e.g., a soft threshold value), and/or the processor circuitry (e.g., a hard threshold value). In such an embodiment, the magnetic localization system may indicate that a distortion is affecting the perceived location of the catheter within the patient upon exceeding the soft threshold value, but continue displaying the perceived location of the catheter on the display. Where the delta value of the index-value exceeds a hard threshold value, the magnetic localization system may no longer update the display with the newly-calculated perceived location of the catheter due to the perceived inaccuracy of the location information. Once the calculated index-value falls back below the hard threshold value, the magnetic localization system will resume updating the display with the perceived location of the catheter within the patient.

As shown in FIG. 3C, a specific experimental/detailed configuration of the sensor coil array 370 is presented. First sensor coil 315 is orientated orthogonal to both second sensor coil 320 and third sensor coil 325. Accordingly, each of the sensor coils is oriented planar to one of three dimensional axes, and receives magnetic field energy that is substantially co-axial with the sensor coil. A center-point of the first coil being 5.596 millimeters (mm) from a center point of the second sensor coil, and the center-point distance between the first and second sensor coils and the third and second sensor coils being 3.006 mm, with an angular offset of the second and third sensor coils relative to the first sensor coil being 22 degrees, and an angular offset of the first and third sensor coils relative to the second sensor coil also being 22 degrees. It is to be understood that various other relative positions and orientations of the sensor coil array can also be utilized.

During operation of the magnetic localization system utilizing a sensor coil array 370 (as shown in FIG. 3C), the calculated magnitude values of the sensed magnetic field rely on the fixed spacing of the sensor coils to determine when magnetic distortion in the magnetic field is resulting in catheter location data that is excessively skewed.

Figure 4:
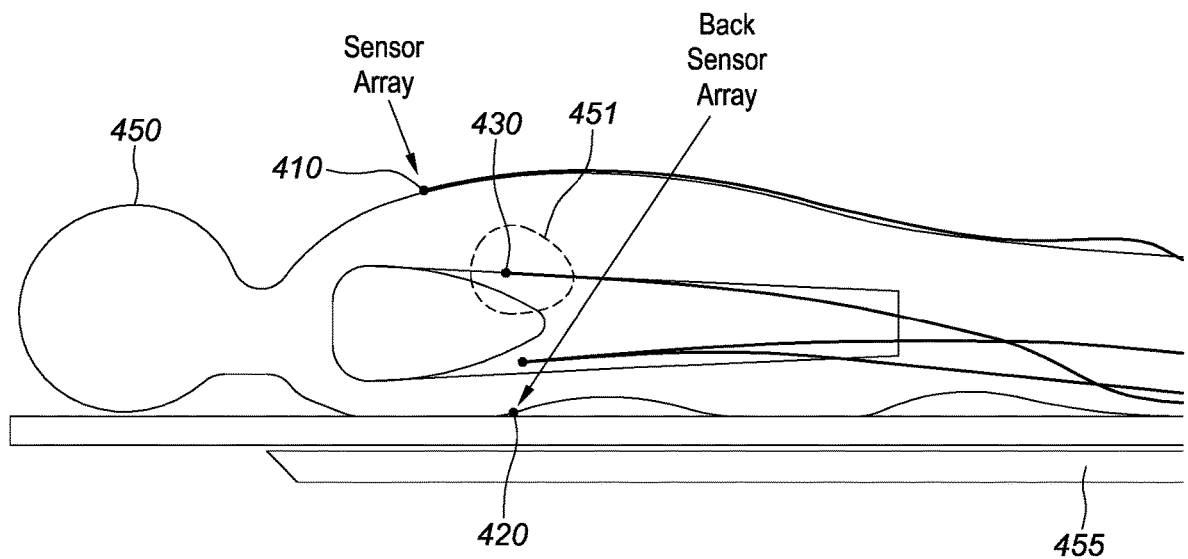
FIG. 4 is an side view of an exemplary placement of magnetic detection sensors on a patient during a medical procedure, consistent with various aspects of the present disclosure.

FIG. 4 shows an exemplary placement of two metal distortion sensors 410 and 420 relative to a patient 450 during a medical procedure where magnetic localization of a medical device within a patient is utilized (e.g., a cardiac ablation procedure). In the present embodiment, the first metal distortion sensor 410 is placed anterior to the patient 450 (e.g., on a patient's chest), while a second metal distortion sensor 420 is placed posterior to the patient (e.g., between a patient's back and an operating table 455). In many exemplary embodiments, the first and second metal distortion sensors are ideally located adjacent (and opposite one another) to the anatomy of the patient where the procedure is being conducted. As shown in FIG. 4, the first and second metal distortion sensors are opposite one another relative to the heart 451, which is receiving treatment by way of catheter 430, which is extended into the heart. Magnetic field transmitters surrounding the patient emit a magnetic field used to determine the position of the catheter. Specifically, the catheter, including a coil in its tip region, senses the magnetic field in proximity to the coil. Processing circuitry can then determine, based on the sensed magnetic field at the tip of the catheter, where the coil is located in the magnetic field and, therefore, where the tip of the catheter is located. However, egress of other ferrous objects into the magnetic field create magnetic distortions within the field that affect localization of the catheter within the field. Accordingly, the first metal distortion sensor 410 detects magnetic distortions in proximity to the anterior of the patient (e.g., medical instruments and equipment), and the second metal distortion sensor 420 detects magnetic distortions in proximity to the posterior of the patient (e.g., ferrous objects associated with the operating room table, or other objects in the magnetic field there below). In such a configuration, magnetic distortions can be identified and a determination can be made as to the effect of the magnetic distortion on the catheter (e.g., whether the magnetic field in proximity to the catheter is being excessively affected by the magnetic distortion).

Figure 5:
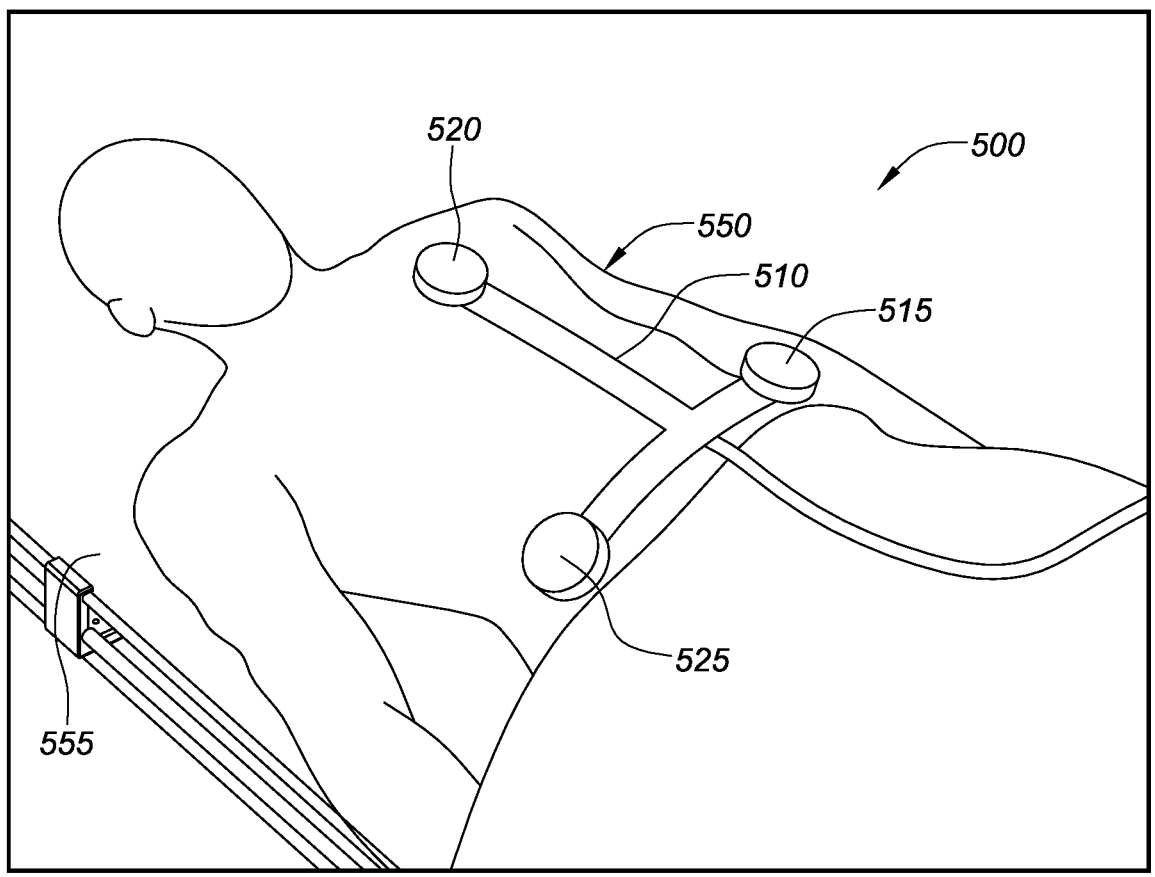
FIG. 5 is an isometric view of a magnetic distortion detection chest fixture on a patient analog, consistent with various aspects of the present disclosure.

FIG. 5 shows an isometric view of a medical operating suite configuration 500 including magnetic distortion detection chest fixture 510 on a patient 550 situated on an operating table 555. As shown in at least one embodiment, the magnetic distortion detection fixture 510 may include three metal distortion sensors 515, 520, and 525. In the present embodiment, the chest fixture 510 is rigid to maintain a constant distance (including position and orientation) between each of the metal distortion sensors. Each of the three metal distortion sensors 515, 520, and 525 can include an array of sensor coils. Each of the sensor coils can be affixed in orthogonal orientations relative to one another. In at least one embodiment, each of the metal distortion sensors 515, 520, and 525 may include an array of three orthogonally orientated and affixed sensor coils, similar to that described and illustrated above in connection with metal distortion sensor 300 (see, e.g., FIGS. 3A and 3B).

During a medical procedure, a chest fixture 510 comprising a plurality of sensor coils is placed within a magnetic field. Each of the respective sensor coils, in each of the respective metal distortions sensors 515, 520, and 525 receive energy indicative of the strength and orientation of the magnetic field. In one specific embodiment, a vector sum of the received energy is computed to determine a perceived change in the position of the sensor coils relative to one another (and/or the perceived change in the position of the metal distortions sensors relative to one another). A perceived change being indicative of a magnetic distortion in the magnetic field proximal to the chest fixture 510.

During operation of the metal distortion sensors 515, 520, and 525 in a magnetic field, the output of each magnetic distortion sensor can be used to calculate magnitude positions and orientations associated with the mechanical position and orientation of the magnetic distortion sensors relative to one another. In one specific embodiment, for example, the vector sum of the distances are calculated between the magnetic distortion sensors. In response to a distortion in the magnetic field, the perceived location of one (or more) of the magnetic distortion sensors may be displaced from its known/fixed location relative to the other magnetic distortion sensors. As a result, the corresponding vector sum would be correspondingly affected. A change in the vector sum from an initial index value, above a determined threshold, is indicative of a distortion to the generated magnetic field. After determining an initial index-value (where the magnetic field is free of distortions), subsequent magnitude positions and orientations may be correlated timewise. These later magnitude values may vary from the initial index-value due to localized magnetic distortions within the magnetic field, resulting in the erroneous reporting of the location and orientation of the magnetic distortion sensors relative to one another (even though the orientation and position of the magnetic distortion sensors, relative to one another, are fixed). The initial index-value may be compared to subsequent index-values to determine when acceptable levels of magnetic field distortion during a medical procedure are exceeded. The delta value (the change in value between the initial index-value and a subsequent index-value) is associated with distortion related drift in the localization of the catheter.

In various embodiments of the present disclosure, to prevent inaccuracies in a magnetic localization system, the magnetic localization system can utilize one or more of the magnetic distortion sensors (e.g., 515, 520, and 525) in the chest fixture 510 to determine a variance between actual locations (based on the known/fixed position of the magnetic distortion sensor within the system) and perceived locations (those determined based on the received magnetic fields at the magnetic distortion sensor and post-processing). The determined variance is indicative of magnetic distortion throughout the magnetic field due to egress of ferrous/metallic objects into the magnetic field. Based on the variance at each of the magnetic distortion sensor locations, a transform may be computed to correct for the distortion at all locations within the magnetic field, including the magnetic distortion experienced by the medical device being magnetically localized.

In various embodiments of a magnetic distortion detection and correction chest fixture, in accordance with the present disclosure, the chest fixture can take a number of various shapes including, for example, a "T" shape, an "X" shape, among other shapes. The shape of the chest fixture being controlled by ideal positioning of the metal distortion sensors at precise locations relative to one another (and within a magnetic field for localizing a medical device therein). The chest fixture can include a varying amount of sensors, including two or more metal distortion sensors. In many embodiments, the metal distortion sensors at least partially encircle the medical device to improve detection of magnetic distortions in proximity to the medical device. Further, in embodiments where fluoroscopy or other X-ray type imaging is required (during a medical procedure), the chest fixture can include materials that are transparent to X-ray imaging, and/or shaped to prevent interference with such imaging.

Figure 6:
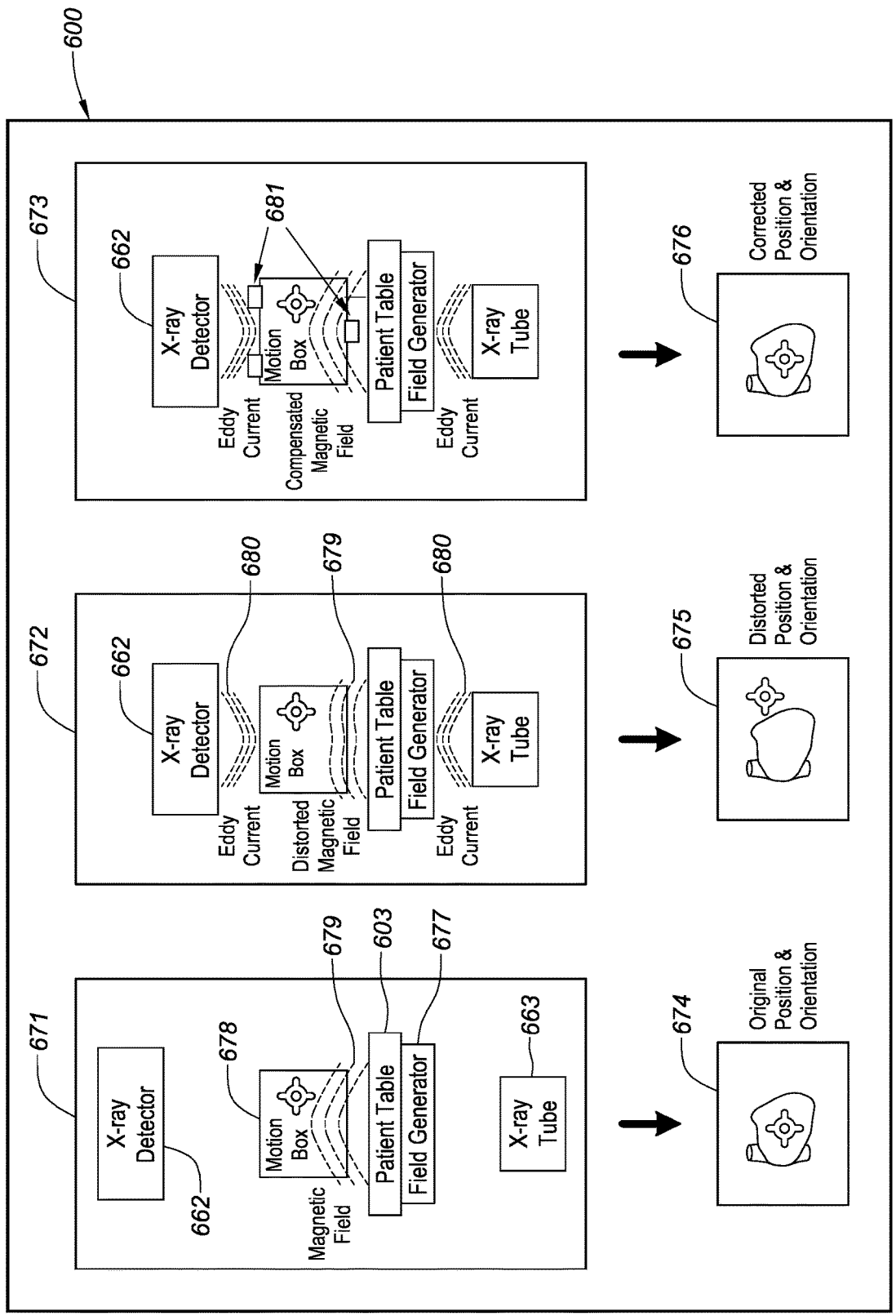
FIG. 6 is a diagram of various operating room suite configurations including a magnetic-based localization system and example localization results for each configuration, consistent with various aspects of the present disclosure.

FIG. 6 is a diagram 600 of various operating room suite configurations including a medical device localization system and exemplary localization results for each configuration. Suite configuration 671 shows X-ray detector 662 and X-ray tube 663 located at nominal positions, where the magnetic components of the X-ray detector and X-ray tube are located far enough from a magnetic field 679 emitted from magnetic field transmitter (field generator) 677 (through patient table 603) is not distorted by these ferrous components. As a result, the localization of an object within motion box 672 (an area within which localization of the medical device can take place) is accurate, as shown in an exemplary display image 674 showing the appropriate position of the object, within the patient's cardiac muscle.

Suite configuration 672 shows X-ray detector 662 and X-ray tube 663 located at undesirable positions, where the magnetic components of the X-ray detector and X-ray tube are located within a magnetic field 679 emitted from magnetic field transmitter (field generator) 677, distorting the magnetic field around motion box 678 via eddy currents 680.

As a result, the localization of an object within the motion box 672 is inaccurate. As shown in exemplary display image 675, even though the localizes object is within the patient's cardiac muscle, the magnetic distortion from the magnetic components within the magnetic field causes the false localization of the object outside of the cardiac muscle.

Suite configuration 673 shows X-ray detector 662 and X-ray tube 663 located at undesirable positions, where the magnetic components of the X-ray detector and X-ray tube are located within a magnetic field 679 emitted from magnetic field transmitter (field generator) 677, distorting the magnetic field in and around motion box 678 via eddy currents 680. As a result, the localization of an object within the motion box 672 is inaccurate. However, each of the magnetic distortion sensors 681 placed around the outer periphery of the motion box 678 detect whether the magnetic field at its known location is distorted. In response to the distortion, a transform can be calculated based on the data provided by the magnetic distortion sensors and applied to the object within the motion box. As shown in exemplary display image 676, even though the localized object is located within a distorted magnetic field, the transform corrects the perceived location of the object and correctly positions it within the patient's cardiac muscle.

Figure 7:
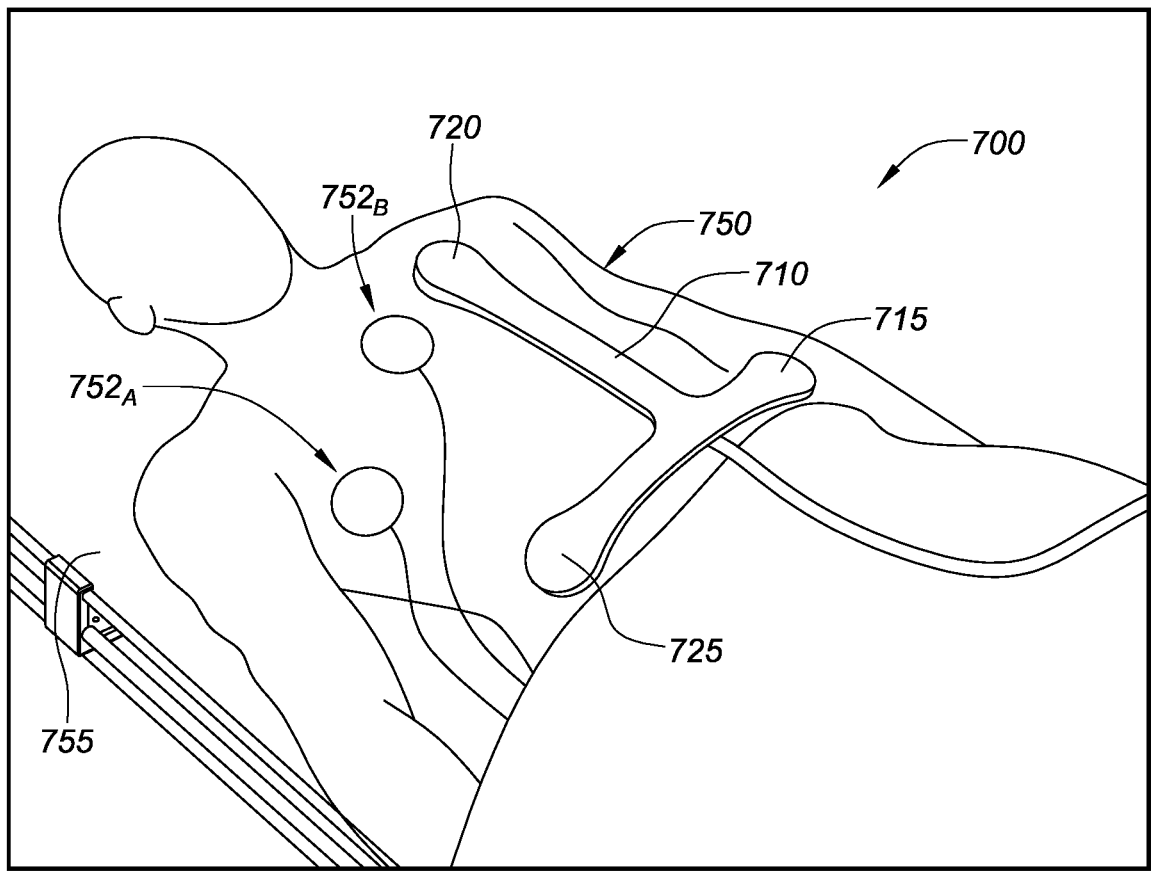
FIG. 7 is an isometric view of a magnetic distortion detection chest fixture on a patient analog, consistent with various aspects of the present disclosure.

FIG. 7 shows an isometric view of a medical operating suite configuration 700 including magnetic distortion detection chest fixture 710 on a patient 750 situated on an operating table 755. The magnetic distortion detection fixture 710 includes three metal distortion sensors 715, 720, and 725. The chest fixture 710 is rigid to maintain a constant distance (including position and orientation) between each of the metal distortion sensors. Each of the three metal distortion sensors 715, 720, and 725 can include an array of sensor coils. Each of the sensor coils can be affixed in orthogonal orientations relative to one another. In the present embodiment, each of the metal distortion sensors 715, 720, and 725 may include an array of three orthogonally orientated and affixed sensor coils, similar to that described and illustrated above in connection with metal distortion sensor 300 (see, e.g., FIGS. 3A and 3B).

During a medical procedure, a chest fixture 710 comprising a plurality of sensor coils is placed within a magnetic field produced by a hybrid localization system for the purposes of detecting a magnetic distortion in proximity to a medical device within a patient 750. A hybrid localization system utilizes both impedance-based and magnetic field-based localization methodologies to more accurately determine the medical devices location. Each of the respective sensor coils, in each of the respective metal distortions sensors 715, 720, and 725, receive energy indicative of the strength and orientation of the magnetic field. A perceived change over time, of the received energy, is indicative of a magnetic distortion in the magnetic field proximal to the chest fixture 710.

In FIG. 7, a magnetic distortion detection chest fixture 710 is implemented with a hybrid localization system, such as the EnSite™ NavX™ Electro Anatomical Mapping System commercially available from St. Jude Medical, Inc. The EnSite™ NavX™ mapping system may utilize both impedance-based and magnetic field-based localization methodologies (e.g., a hybrid system). Impedance measuring patches $752_{A-B}$ are electrically coupled to the patient. In some implementations of the EnSite™ NavX™ mapping system, the impedance measuring patches $752_{A-B}$ are placed on a patient's chest (e.g., $752_B$), on either side of patient's chest (e.g., $752_A$), and on at least one of patient's legs. Based on the varying impedance values detected by the impedance measuring patches $752_{A-B}$, an impedance-based location of the medical device may be determined.

In the embodiment of FIG. 7, the chest fixture 710 enables improved accuracy within the system by indicating when a location of the medical device provided by the magnetic field-based localization system is inaccurate due to a magnetic distortion. In response, the mapping system may ignore the location data from the magnetic field-based portion of the system, or correct for the distortion using one or more of the methods disclosed herein. For example, data from one or more of the magnetic distortion sensors (e.g., 715, 720, and 725) in the chest fixture 710 may be used to determine a variance between actual locations (based on the known/fixed position of the magnetic distortion sensor within the system) and perceived locations (those determined based on the received magnetic fields at the magnetic distortion sensor and post-processing). The determined variance is indicative of magnetic distortion throughout the magnetic field due to egress of ferrous/metallic objects into the magnetic field. Based on the variance at each of the magnetic distortion sensor locations, a transform may be computed to correct for the distortion at all locations within the magnetic field, including the magnetic distortion experienced by the medical device being magnetically localized.

In further more specific embodiments of the present disclosure, and consistent with all the above embodiments, magnetic distortion sensors (and the sensor coils therein) may also be utilized to compensate for the sensed magnetic distortion. To compensate for magnetic distortion in the magnetic localization system, the fixed locations of the magnetic distortion sensors provide a fixed reference frame. Based on the variance between the actual position (a known position or a position detected during calibration) and the perceived location of each of the magnetic distortion sensors based upon the sensed magnetic field, the effect of the magnetic distortion throughout the magnetic field may be calculated and represented by a transform that restores the perceived locations of each of the magnetic distortion sensors back to the respective actual positions. Similarly, the transform may be applied to the perceived location of a medical device within the magnetic field to determine a corrected (actual) location of the medical device.

Where an actual location of a magnetic distortion sensor in a reference frame is not known (such as where the fixture is fixed to the patient), the relative location of the magnetic distortion sensor to another magnetic distortion sensor, where the distance between the two magnetic distortion sensors is fixed, can also be relied upon to correct for magnetic distortion in a magnetic localization system. The transform in such an embodiment being based upon a variance between the actual distances between the magnetic distortions sensors and the perceived distances between the magnetic distortions sensors based upon the sensed magnetic field at each of the magnetic distortion sensors. The calculated transform may then be used to correct the perceived location of the medical device.

In embodiments such as those presented in FIG. 5, the magnetic distortion sensors 515, 520, and 525 are generally centered about the portion of the patient's body where the medical device localization is to take place. For example, in a cardiac-related operation, the magnetic distortion sensors are desirably positioned in close proximity to the patient's heart to improve detection of magnetic distortions affecting the medical device therein.

In view of the present disclosure, various other configurations of a chest fixture for magnetic distortion detection and correction within a magnetic localization system for use during a medical procedure are readily envisioned. For example, in one embodiment, the chest fixture is positioned on a patient analog to replicate the positioning of the chest fixture and other leads/pads (e.g., electrocardiography ("ECG") pads, impedance-based localization system pads, among others) on a patient for an intracardiac procedure. The chest fixture may be generally situated on a patient's chest in proximity to the area of the patient where magnetic localization is to take place (e.g., a target area). In more specific embodiments, the magnetic distortion sensors at each end of the chest fixture encircle the target area to maximize magnetic distortion detection, which can emanate from a multitude of locations within the operating room.

In some embodiments, a chest fixture for magnetic distortion detection and correction within a magnetic localization system may be formed of a rigid material, such as a plastic. As discussed above, to detect and correct for magnetic distortions, fixed positions between the magnetic distortions sensors in the chest fixture minimize error associated with variation in the interstitial spacing between the magnetic distortion sensors. However, aspects of the present disclosure may also implement semi-fixed arrangements of the magnetic distortion sensors.

In various implementations of a chest fixture for magnetic distortion detection and correction, where applications require the use of fluoroscopy or other X-ray type imaging, the chest fixture may be comprised (to the extent possible) with X-ray translucent materials to limit chest fixture exposure in the resulting images.

It should be readily understood that a chest fixture, as disclosed herein, may take a number of varying shapes and sizes, and comprise one or more magnetic distortion sensors. The configurations disclosed in, for example, FIGS. 5 and 7 are intended to show one example embodiment of such a chest fixture with an array of magnetic distortion sensors, and is not at all intended to limit the multitude of shapes and sizes such a chest fixture could take.

Specific algorithms used in conjunction with the metal distortion sensors and processing circuitry for determining the existence of magnetic distortions within the magnetic field and the effect of the magnetic distortion on magnetic localization of the catheter 430 within the magnetic field are presented below. Based on the specific/experimental metal distortion detection algorithms disclosed below, one of skill in the art is readily capable of deriving numerous detection algorithm variations hereto.

Specific/Experimental Metal Distortion Detection Algorithms

In a first specific/experimental metal distortion detection algorithm, sensor coil array(s) are assigned a magnitude value correlated with vector distance between individual sensors. Subsequent values and/or changes from index values are used to determine whether the system is operating within acceptable levels of magnetic field distortion/interference. For purposes of the present disclosure, this value is described as the Metal Distortion Sensor ("MDS") value. In the present specific/experimental embodiment, the sensor coil array includes three sensor coils; however, various other embodiments may be readily implemented, in view of the present disclosure, that utilize sensor coil arrays with one or more sensor coils.

Metal distortion detection is achieved by observing the amount of shift seen in the position data of the catheters and correlating it to an amount of shift seen in the MDS. The MDS value is calculated from the three 5 degree of freedom (A, B and C) sensors of the MDS assembly and calculated by the equation below. In view of the following, a skilled artisan would readily be able to craft algorithms for applications using more than one metal distortion sensor.

$$MDS1 = AB + BC + CA$$

$$AB = \sqrt{(ATx-BTx)^2 + (ATy-BTy)^2 + (ATz-BTz)^2}$$

$$BC = \sqrt{(BTx-CTx)^2 + (BTy-CTy)^2 + (BTz-CTz)^2}$$

$$CA = \sqrt{(CTx-ATx)^2 + (CTy-ATy)^2 + (CTz-ATz)^2}$$

Shift between 2 points is calculated per the Euclidean distance equation:

$$MDS\ Delta = \sqrt{(x_1-x_2)^2 + (y_1-y_2)^2 + (z_1-z_2)^2}$$

where x1, y1, z1 is the P&O data from the baseline location and x2, y2, z2 is the P&O data from the measured data point. MDS Delta=|MDS Measured Value at given shift−MDS Baseline Value.

Through characterization in typical application environments, one can correlate the amount of change in the MDS value (MDS Delta) and a shift in the perceived location of an intracardiac catheter due to the magnetic field distortion. The value defined above is calculated using only 3 (Tx, Ty, Tz) out of the 5 degrees of freedom.

In a second specific/experimental metal distortion detection algorithm, all 5 degrees of freedom of the three sensors coils (A, B and C) of the metal distortion sensor are utilized. Specifically, the algorithm takes into account Tx, Ty, Tz, Dx, Dy, Dz where (Dx,Dy, Dz) denotes the unit vector to which a sensor coil (A, B, or C) is directed. The algorithm defines indexes which measure changes in the mechanical properties of the metal distortion sensor between baseline position and a later data point, and then uses a weighting on these indexes to return a value (MDS2) used to determine acceptable levels of magnetic field distortion/interference, and/or change in the magnetic field.

In the second specific/experimental metal distortion detection algorithm, P&O_ref is data measured at a reference event and P&O_dp is data measured at a later data point event. Specifically, $$P\&O_{Ref} \begin{pmatrix} ATx_{ref} & ATy_{ref} & ATz_{ref} & ADx_{ref} & ADy_{ref} & ADz_{ref} \\ BTx_{ref} & BTy_{ref} & BTz_{ref} & BDx_{ref} & BDy_{ref} & BDz_{ref} \\ CTx_{ref} & CTy_{ref} & CTz_{ref} & CDx_{ref} & CDy_{ref} & CDz_{ref} \end{pmatrix}$$

and $$P\&O_{dp} \begin{pmatrix} ATx_{dp} & ATy_{dp} & ATz_{dp} & ADx_{dp} & ADy_{dp} & ADz_{dp} \\ BTx_{dp} & BTy_{dp} & BTz_{dp} & BDx_{dp} & BDy_{dp} & BDz_{dp} \\ CTx_{dp} & CTy_{dp} & CTz_{dp} & CDx_{dp} & CDy_{dp} & CDz_{dp} \end{pmatrix}$$

The indexes k1, k2, k3, k4, k5, k6 are calculated using:

$$f1[T_{dp}, T_{ref}] = \left\{ \frac{\text{Norm}\lfloor AT_{dp} - BT_{dp} \rfloor}{\text{Norm}\lfloor AT_{ref} - BT_{ref} \rfloor} - 1, \frac{\text{Norm}\lfloor AT_{dp} - CT_{dp} \rfloor}{\text{Norm}\lfloor AT_{ref} - CT_{ref} \rfloor} - 1, \frac{\text{Norm}\lfloor BT_{dp} - CT_{dp} \rfloor}{\text{Norm}\lfloor BT_{ref} - CT_{ref} \rfloor} - 1 \right\}$$

$$f2[D_{dp}, D_{ref}] = \{\langle AD_{dp}, BD_{dp} \rangle - \langle AD_{ref}, BD_{ref} \rangle, \langle AD_{dp}, CD_{dp} \rangle - \langle AD_{ref}, CD_{ref} \rangle, \langle BD_{dp}, CD_{dp} \rangle - \langle BD_{ref}, CD_{ref} \rangle\}$$

-continued $$f3[D_{dp}, D_{ref}, m, n] = \text{Abs}\left[\text{Abs}\left[\text{Determinant}\begin{bmatrix}AD_{dp}\\BD_{dp}\\CD_{dp}\end{bmatrix}\right]^m - \text{Abs}\left[\text{Determinant}\begin{bmatrix}AD_{ref}\\BD_{ref}\\CD_{ref}\end{bmatrix}\right]^m\right]^{\frac{1}{n}}$$

$$g1[x, y, z] = (x^2 + y^2 + z^2)^{1/2}$$

$$g2[x, y, z] = \text{Abs}[xy + xz + yz]$$

$$g3[x, y, z] = \text{Abs}[xyz]$$

$$g4[x, m, n] = (1 + (\text{Abs}[x])^{1/m})^{-n}$$

$$A1 = f1[T_{dp}, T_{ref}],$$

$$A2 = f2[T_{dp}, T_{ref}],$$

$$b12 = g2[A1],$$

$$b13 = g3[A1],$$

$$b22 = g2[A2]$$

$$k1 = g4[b13, 2, 2],$$

$$k2 = g4[b22, 2, 2]$$

$$k3 = g4[b12, 2, 2],$$

$$k4 = g1[A2],$$

$$k5 = f3[D_{dp}, D_{ref}, 2, 2],$$

$$k6 = f3[D_{dp}, D_{ref}, 4, 4]$$

MDS2 is then calculated using system calibration weights specific to the system setup (e.g., relative position of patient to metal distortion sensor, relative position of sensor to magnetic field source, etc.), w1, w2, w3, w4, w5, and w6:

$$\text{MDS2} = \text{Abs}[w1*k1 + w2*k2 + w3*k3 + w4*k4 + w5*k5 + w6*k6]$$

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

What is claimed is:

1. A method for detecting magnetic distortion in a magnetic field for localization of a catheter within a patient, the method including:
   receiving a first set of one or more signals from a metal distortion detection fixture indicative of the magnetic field sensed by each of a plurality of sensor coils within the metal distortion detection fixture at a first time, wherein a position of the metal distortion detection fixture is located within the magnetic field,
   determining a first magnitude value of first combined signals indicative of a magnetic field at the first time,
   receiving a second set of one or more signals from the metal distortion detection fixture indicative of the magnetic field sensed by each of the plurality of sensor coils at a second time,
   determining a second magnitude value of second combined signals indicative of another magnetic field at the second time,
   determining a magnetic shift in the magnetic field between the first and second magnitude values,
   comparing the magnetic shift to a threshold shift amount indicative of a magnetic distortion in the magnetic field,
   determining whether the magnetic shift is indicative of a ferrous object within the magnetic field when the magnetic shift is greater than the threshold shift amount, and
   detecting a variance between a perceived location of the catheter within the patient and an actual location in an output from the metal distortion detection fixture in response to the magnetic shift being greater than the threshold shift amount.

2. The method of claim 1, further including, in response to a determination that the magnetic shift is greater than the threshold shift amount indicative of a magnetic distortion in the magnetic field, disregarding the perceived location of the catheter calculated during the threshold shift amount.

3. The method of claim 1, further including, in response to a determination that the magnetic shift is greater than the threshold shift amount indicative of a magnetic distortion in the magnetic field, outputting a sensory indication to a clinician of the magnetic distortion.

4. The method of claim 1, further including
   positioning the metal distortion detection fixture posterior to the patient's chest cavity; and
   providing a second metal distortion detection fixture positioned anterior to the patient's chest cavity.

5. The method of claim 1, wherein the steps of determining the first and second magnitude values further includes determining the magnitude values using the equation:

$$MDS1 = AB + BC + CA$$

$$AB = \sqrt{(ATx-BTx)^2 + (ATy-BTy)^2 + (ATz-BTz)^2}$$

$$BC = \sqrt{(BTx-CTx)^2 + (BTy-CTy)^2 + (BTz-CTz)^2}$$

$$CA = \sqrt{(CTx-ATx)^2 + (CTy-ATy)^2 + (CTz-ATz)^2}$$

where MDS1 is the magnitude value, AB is a first vector distance between first and second sensor coils of the metal distortion detection fixture, BC is a second vector distance between the second and a third sensor coils of the metal distortion detection fixture, and CA is a third vector distance between the first and the third sensor coils of the metal distortion detection fixture.

6. The method of claim 1, wherein the magnetic shift is determined by the equation:

$$\text{MDS Delta} = \sqrt{(x_1-x_2)^2 + (y_1-y_2)^2 + (z_1-z_2)^2}$$

where x1, y1, z1 is position and orientation data of sensor coils of the metal distortion fixture from the first time, and x2, y2, z2 is position and orientation data of the sensor coils from the second time, and the magnetic shift is directly correlated to a perceived change in location of the catheter within the patient due to the magnetic shift.

7. The method of claim 1, wherein the magnetic distortion fixture includes three sensor coils, wherein each magnitude value of the three sensor coils are determined by the equation:

$$P\&O_{Ref} \begin{pmatrix} ATx_{ref} & ATy_{yef} & ATz_{ref} & ADx_{ref} & ADy_{ref} & ADz_{ref} \\ BTx_{ref} & BTy_{ref} & BTz_{ref} & BDx_{ref} & BDy_{ref} & BDz_{ref} \\ CTx_{ref} & CTy_{ref} & CTz_{ref} & CDx_{ref} & CDy_{ref} & CDz_{ref} \end{pmatrix}$$

$$P\&O_{dp} \begin{pmatrix} A\gamma x_{dp} & ATy_{dp} & ATz_{dp} & ADx_{dp} & APy_{dp} & ADz_{dp} \\ BTx_{dp} & BTy_{dp} & BTz_{dp} & BDx_{dp} & BDy_{dp} & BDz_{dp} \\ CTx_{dp} & CTy_{dp} & CTz_{dp} & CDx_{dp} & CDy_{dp} & CDz_{dp} \end{pmatrix}$$

wherein indexes k1, k2, k3, k4, k5, k6 are calculated using:

$$f1[T_{dp}, T_{ref}] = \left\{ \frac{\text{Norm}\lfloor AT_{dp} - BT_{dp} \rfloor}{\text{Norm}\lfloor AT_{ref} - BT_{ref} \rfloor} - 1, \frac{\text{Norm}\lfloor AT_{dp} - CT_{dp} \rfloor}{\text{Norm}\lfloor AT_{ref} - CT_{ref} \rfloor} - 1, \frac{\text{Norm}\lfloor BT_{dp} - CT_{dp} \rfloor}{\text{Norm}\lfloor BT_{ref} - CT_{ref} \rfloor} - 1 \right\}$$

$$f2[D_{dp}, D_{ref}] =$$

$$\{\langle AD_{dp}, BD_{dp}\rangle - \langle AD_{ref}, BD_{ref}\rangle, \langle AD_{dp}, CD_{dp}\rangle - \langle AD_{ref}, CD_{ref}\rangle, \langle BD_{dp}, CD_{dp}\rangle - \langle BD_{ref}, CD_{ref}\rangle\}$$

-continued $$f3[D_{dp}, D_{ref}, m, n] = \text{Abs}\left[\left[\text{Abs}\left[\text{Determinant}\begin{bmatrix} AD_{dp} \\ BD_{dp} \\ CD_{dp} \end{bmatrix}\right]\right]^m - \text{Abs}\left[\text{Determinant}\begin{bmatrix} AD_{ref} \\ BD_{ref} \\ CD_{ref} \end{bmatrix}\right]^m\right]^{\frac{1}{n}}$$

$$g1[x, y, z] = (x^2 + y^2 + z^2)^{1/2}$$

$$g2[x, y, z] = \text{Abs}[xy + xz + yz]$$

$$g3[x, y, z] = \text{Abs}[xyz]$$

$$g4[x, m, n] = (1 + (\text{Abs}[x])^{1/m})^{-n}$$

$$A1 = f1[l_{dp}, T_{ref}],$$

$$A2 = f2[T_{dp}, T_{ref}],$$

$$b12 = g2[A1],$$

$$b13 = g3[A1],$$

$$b22 = g2[A2]$$

$$k1 = g4[b13, 2, 2],$$

$$k2 = g4[b22, 2, 2],$$

$$k3 = g4[b12, 2, 2],$$

$$k4 = g1[A2],$$

$$k5 = f3[D_{dp}, D_{ref}, 2, 2],$$

$$k6 = f3[D_{dp}, D_{ref}, 4, 4]$$

$$MDS2 = \text{Abs}[w1*k1 + w2*k2 + w3*k3 + w4*k4 + w5*k5 + w6*k6]$$

where P&O_ref is the data measured at the first time, P&O_dp is the data measure at the second time, MDS2 is the magnitude value, AB is a first vector distance between first and second sensor coils, BC is a second vector distance between the second sensor coil and a third sensor coil, CA is a third vector distance between the first sensor coil and the third sensor coil, Tx, Ty, Tz, Dx, Dy, Dz are the five degrees of freedom of the metal distortion detection fixture, (Dx, Dy, Dz) denotes the unit vector to which one of the three sensor coils (A, B or C) is directed, and w1, w2, w3, w4, w5, and w6 are system calibration weights specific to the system.

8. The method of claim 7, wherein the indexes are weighted to determine the MDS2 magnitude value, wherein the MDS2 magnitude value correlates to a change in the mechanical properties of the metal distortion detection fixture between the first and second times.

9. The method of claim 1, further including, in response to the determination that the magnetic shift is greater than the threshold shift amount indicative of a magnetic distortion in the magnetic field, correcting the localization of the catheter using a base model-function that for each input of the perceived position and orientation of the catheter generates a corrected position and orientation of the catheter, in at least partial reliance on the fixed position between the metal distortion detection fixture and a magnetic field generator, and the fixed distances and orientations of the plurality of sensor coils relative to one another within the metal distortion detection fixture.

10. The method of claim 1, further including, in response to the determination that the magnetic shift is greater than the threshold shift amount indicative of a magnetic distortion in the magnetic field, correcting the localization of the catheter using a base model-function that for each input of the perceived location and orientation of the catheter generates a corrected position and orientation of the catheter, and the model-function satisfies time-dependent relative fixed distances and orientations of sensors coil within the metal distortion detection fixture to other time-dependent measurements.

11. The method of claim 1, further comprising: computing a transform to correct for the detected variance between the perceived location of the catheter within the patient and the actual location in the output from the metal distortion detection fixture.

12. The method of claim 11, wherein the transform corrects for the magnetic distortion at the perceived location of the catheter.

* * * * *